United States Patent
Chodavarapu

(10) Patent No.: US 10,488,339 B2
(45) Date of Patent: Nov. 26, 2019

(54) FREQUENCY DOMAIN FLUORESCENCE MEASUREMENT SYSTEM

(71) Applicant: University of Dayton, Dayton, OH (US)

(72) Inventor: Vamsy Chodavarapu, Beavercreek, OH (US)

(73) Assignee: University of Dayton, Dayton, OH (US)

( * ) Notice: Subject to any disclaimer, the term of this patent is extended or adjusted under 35 U.S.C. 154(b) by 0 days.

(21) Appl. No.: 16/292,996

(22) Filed: Mar. 5, 2019

(65) Prior Publication Data

US 2019/0277763 A1  Sep. 12, 2019

Related U.S. Application Data

(60) Provisional application No. 62/639,177, filed on Mar. 6, 2018.

(51) Int. Cl.
*G01N 21/64* (2006.01)

(52) U.S. Cl.
CPC ..... *G01N 21/6428* (2013.01); *G01N 21/6408* (2013.01); *G01N 2021/6439* (2013.01); *G01N 2201/061* (2013.01)

(58) Field of Classification Search
CPC ........... G01N 21/6428; G01N 21/6408; G01N 2201/061; G01N 2021/6439; G01N 21/64; G01N 15/14; G01J 9/00; A61B 5/14
See application file for complete search history.

(56) References Cited

U.S. PATENT DOCUMENTS

| 4,840,485 A | 6/1989 | Gratton |
| 2014/0080225 A1 | 3/2014 | Chodavarapu et al. |
| 2016/0033413 A1 | 2/2016 | Chodavarapu et al. |
| 2016/0266087 A1* | 9/2016 | Lo ...................... G01N 33/4833 |

* cited by examiner

*Primary Examiner* — Abdullahi Nur
(74) *Attorney, Agent, or Firm* — Wood Herron & Evans LLP

(57) ABSTRACT

Apparatuses, methods, and computer program products for analyzing target compounds. An excitation signal comprising light having a time-varying intensity is transmitted into a target compound. In response to receiving the excitation signal, the target compound generates an emission signal. To increase the intensity of the emission signal, a fluorophore may be provided to the target compound. The fluorophore may be configured to react with a characteristic of the target compound so that the fluorophore generates the emission signal in response to the presence of both the characteristic and the excitation signal. The emission signal may be compared to the excitation signal in a frequency domain to determine a phase of the emission signal relative to the excitation signal. The phase may be used to determine a luminescence lifetime of the emission signal. If the detected luminescence lifetime matches an expected luminescence lifetime, the target compound likely includes the characteristic.

20 Claims, 4 Drawing Sheets

FREQUENCY DOMAIN FLUORESCENCE MEASUREMENT SYSTEM

CROSS-REFERENCE TO RELATED APPLICATIONS

This application claims the benefit of U.S. Application No. 62/639,177 filed on Mar. 6, 2018, and entitled "A Frequency Domain Fluorescence Measurement System", the disclosure of which is incorporated by reference herein in its entirety.

FIELD OF THE INVENTION

This invention generally relates to fluorometry, and more particularly, to methods, systems, and computer program products for measuring fluorescence in the frequency domain.

BACKGROUND

Conventional sensors used to determine a chemical or biological characteristic of a target compound rely measuring emission signals emitted by the target compound in response to an excitation signal incident on the target compound. In some cases, a fluorophore is added the target compound to increase the intensity of the emission signal. A reaction of the target compound to the fluorophore may be characterized by an optical emission signal generated by target compound in response to the excitation signal. The characteristics of the target compound can then be determined based on the emission signal. In other cases, the emission signal may be an attenuated version of excitation signal received after passing through or being reflected by the target compound. One example of an attenuation-based measurement involves transmitting the excitation signal into a blood sample and determining the oxygen level of the blood sample based on the intensity of the emission signal, i.e., the optical signal that emerges from the sample. This type of optical measurement focuses on how the target compound attenuates the emission signal. In either case, the intensity of the optical signal emitted by the target compound is used to identify the characteristics of the target compound.

One disadvantage of intensity measurements is that they are susceptible to aging of the detector electronics, varying ambient conditions, and environmental noise. The resulting fluctuations in the detected intensity of the emission signal may produce inaccurate results. Further, each time the excitation signal is introduced into the target compound, the optical characteristics of the target compound can change, e.g., due to bleaching of the target compound or fluorophore. This degradation may cause the intensity of the emission signal to vary so that it is no longer able to provide accurate information regarding the characteristics of the target compound.

Another way to characterize a target compound is to measure an excited state lifetime of the emission signal. This method also involves using an excitation signal to excite fluorescent receptors in the target compound, which can include an inherent fluorophore in the target compound or a fluorophore introduced into the target compound, and detecting an emission signal emitted by the excited fluorescent receptors. The excited state lifetime of the fluorescent receptor is then determined based on the behavior of the emission signal and used to identify the characteristics of the target compound. Unlike the absolute intensity of the emission signal, the excited state lifetime of the target compound is not impacted by changes in the detector electronics, ambient conditions, or environmental noise. The excited state lifetime is also unaffected by bleaching. Thus, using an excited state lifetime to characterize a target compound can provide more accurate results as compared to simple optical signal intensity-based measurements.

Conventional excited state lifetime measurements monitor a decay in the emission signal as the excitation signal interacts with the target compound, with the rate of decay in the emission signal being indicative of the characteristics of the target compound. For example, one type of characteristic of the target compound may be identified for a relatively long excited state lifetime (e.g., ≥100 ns) as determined from a correspondingly slower decay rate of the emission signal. Another characteristic of the target compound may be indicated by a relatively short excited state lifetime, e.g., ≤50 ns.

One problem with conventional excited state lifetime monitoring systems is that they are limited to monitoring relatively long excited state lifetimes, which restricts the type of fluorescent receptors that can be monitored. Monitoring the duration of the excited state lifetime also requires electronics that compute at extremely fast rates to capture the excited state lifetime of the fluorophore before the excited state lifetime expires. Such electronics significantly increase the cost of these systems as well as the space that the systems occupy. Moreover, these large and costly systems are still are unable to detect excited state lifetimes below about 100 ns. Thus, conventional excited state lifetime monitoring systems are limited in the types of fluorescent receptors that can be used and in turn are limited in the types of chemical or biological characteristics that can be identified.

Thus, there is a need for improved apparatuses, methods, and computer program products for performing optical analysis of target compounds, and specifically, that accurately determine excited state lifetimes of the target compounds, particularly those having short durations.

SUMMARY

In an embodiment of the invention, an apparatus for analyzing a target compound is provided. The apparatus includes a light source configured to generate an excitation signal, a photodetector configured to receive an emission signal, and one or more processors operably coupled to the light source and the photodetector. The one or more processors are configured to cause the apparatus to transmit the excitation signal into the target compound, receive the emission signal from the target compound, compare the emission signal to the excitation signal in a frequency domain, and determine a phase of the emission signal relative to the excitation signal based on the comparison. The one or more processors are further configured to determine a first luminescence lifetime based on the phase of the emission signal, and in response to the first luminescence lifetime matching a second luminescence lifetime, determine that the target compound includes a predetermined characteristic.

In another embodiment of the invention, a method of analyzing the target compound is provided. The method includes transmitting the excitation signal into the target compound, receiving the emission signal from the target compound, comparing the emission signal to the excitation signal in the frequency domain, and determining the phase of the emission signal relative to the excitation signal based on the comparison. The method further includes determining the first luminescence lifetime based on the phase of the emission signal, and in response to the first luminescence lifetime matching the second luminescence lifetime, determining that the target compound includes the predetermined characteristic.

In another embodiment of the invention, a computer program product for analyzing the target compound is provided. The computer program product includes a non-transitory computer-readable storage medium, and program code stored on the non-transitory computer-readable storage medium. The program code is configured so that, when executed by one or more processors, the program code causes the one or more processors to transmit the excitation signal into the target compound, receive the emission signal from the target compound, compare the emission signal to the excitation signal in the frequency domain, and determine the phase of the emission signal relative to the excitation signal based on the comparison. The program code further causes the one or more processors to determine the first luminescence lifetime based on the phase of the emission signal, and, in response to the first luminescence lifetime matching a second luminescence lifetime, determine that the target compound includes a predetermined characteristic.

The above summary presents a simplified overview of some embodiments of the invention to provide a basic understanding of certain aspects of the invention discussed herein. The summary is not intended to provide an extensive overview of the invention, nor is it intended to identify any key or critical elements, or delineate the scope of the invention. The sole purpose of the summary is merely to present some concepts in a simplified form as an introduction to the detailed description presented below.

BRIEF DESCRIPTION OF THE DRAWINGS

The accompanying drawings, which are incorporated in and constitute a part of this specification, illustrate various embodiments of the invention and, together with the general description of the invention given above, and the detailed description of the embodiments given below, serve to explain the embodiments of the invention.

DETAILED DESCRIPTION

Embodiments of the invention include a frequency domain fluorescence measurement system for analyzing a target compound to determine one or more characteristics of the target compound. Exemplary characteristics may include one or more chemical or biological characteristics, e.g., a presence or an amount of a chemical or biological material in the target compound. The system may include an excitation and detection device that generates an excitation signal. The excitation signal may be an optical signal that is provided to the target compound through an optical sensor film which interfaces with the target compound. The excitation signal may include a frequency component that corresponds to or excites a resonant frequency of a fluorophore which may be inherent to the target compound or may have been provided to the target compound. The fluorophore may be a fluorescent chemical compound that re-emits light in response to being excited by the excitation signal, wherein the emitted light indicates the presence or characteristic of the target compound. Thus, in response to being exposed to the excitation signal, the fluorophore may emit an emission signal at the resonant frequency.

The emission signal generated by the excited fluorophore may propagate from the target compound through the optical sensor film before being detected by the excitation and detection device. The excitation and detection device may compare the received emission signal to the excitation signal and determine a phase shift between these signals in the frequency domain. The excitation and detection device may then determine a luminescence lifetime of the fluorophore based on the phase shift between the excitation signal and the emission signal.

The duration of the luminescence lifetime as determined by the phase shift between the excitation signal and the luminescence signal may provide an indication of one or more characteristics of the target compound. Advantageously, the luminescence lifetimes detectable by embodiments of the invention may be significantly shorter than the excited state lifetimes detectable by conventional monitoring systems. This improvement may, in turn, significantly increase the types of chemical or biological characteristics that can be identified as compared to conventional systems.

Figure 1:
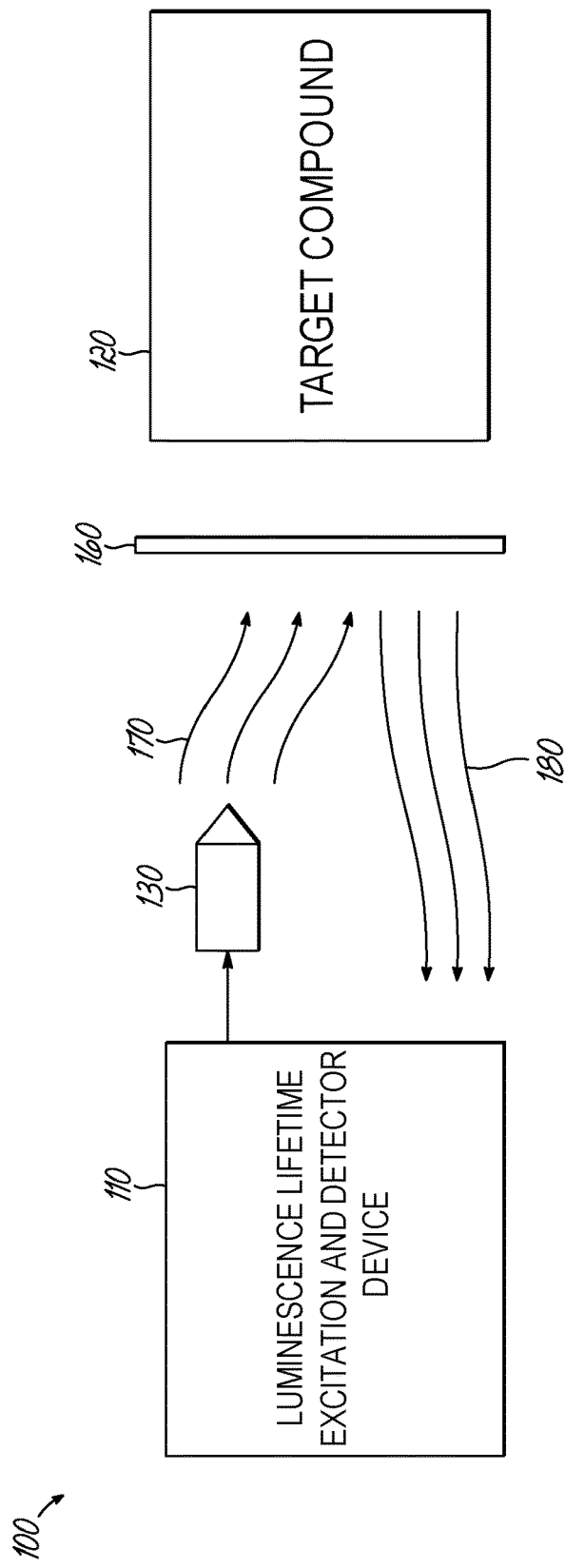
FIG. 1 is a diagrammatic view of an exemplary frequency domain fluorescence measurement system that may be used to analyze a target compound.

FIG. 1 depicts a frequency domain fluorescence measurement system 100 that may be used to analyze a target compound 120 in accordance with an embodiment of the invention. The frequency domain fluorescence measurement system 100 may include an excitation and detection device 110, a light source 130 configured to emit an excitation signal 170, and an optical sensor film 160. The optical sensor film 160 may include one or more fluorophores configured provide a fluorescent indicator that emits an emission signal 180 when exposed to the excitation signal 170 in the presence of one or more predetermined chemical or biological materials or other predetermined characteristic of the target compound. In an alternative embodiment of the invention, the target compound 120 may inherently luminesce in response to receiving the excitation signal 170, or may include a fluorophore that has been added thereto. In either case, the optical sensor film 160, or fluorophores in the film, may be omitted. Thus, it should be understood that embodiments of the invention are not limited to any particular method of providing a fluorophore to the target compound, or the analysis of target compounds that require the addition of fluorophores.

The target compound 120 may be a sample of a material that includes chemical or biological characteristics that a user wishes to identify. The sample could be an air sample, water sample, or biological sample, to name but a few. For example, the user may wish to determine a blood oxygen level of a blood sample, in which case the blood sample would be the target compound 120 and the blood oxygen level would be the characteristic of the target compound that the user wishes to determine. In order to determine the characteristic, a fluorophore may be added to or otherwise provided to the target compound 120. One way of providing the fluorophore may by be including the fluorophore on a surface of the optical sensor film 160 that comes into contact with the target compound. In other cases, the fluorophore may be injected into or otherwise mixed with the target compound.

The fluorophore provided to the target compound 120 may be selected based on a luminescence lifetime of the fluorophore when it is provided to the target compound 120 having the characteristics in question and excited by the excitation signal 170. The excitation signal 170 may comprise electromagnetic radiation (e.g., ultraviolet light) having a time-varying intensity. The intensity of the excitation signal 170 may be modulated using a suitable waveform, e.g., a waveform including one or more sinusoidal frequency components. An exemplary modulation signal is provided by equation 1 below:

$$(\sin(2\pi f) + C) \quad \text{(Eqn. 1)}$$

where f is the frequency of the frequency component (sometimes referred to herein as the frequency of the excitation signal 170), and C is an offset that may be used to control a modulation index of the excitation signal 170, e.g., to prevent the modulation signal from having a negative value. The modulation signal may be used to drive the light source 130 so that the light source 130 emits light having an intensity proportional to the modulation signal.

The luminescence lifetime may be related to an amount of time that the fluorophore emits an emission signal 180 after being excited by the excitation signal 170. The emission signal 180 may be produced by the luminescence generated by the fluorophore when excited by the excitation signal 170. The frequency of the excitation signal 170 may be selected to interact with the characteristics of the target compound 120. Specific characteristics of the target compound 120 may then be identified based on the emission signal 180. Appropriate fluorophores may include a fluorophore that is both excited by the excitation signal 170, and that generates an emission signal 180 with a luminescence lifetime that identifies the characteristic being measured. That is, to detect a particular characteristic of the target compound 120 being tested, an appropriate fluorophore as well as an excitation signal 170 including an appropriate frequency component may need to be used to generate an emission signal 180 with a luminescence lifetime that identifies the particular characteristic.

For example, if the user wishes to identify the blood oxygen level of the blood sample, they may select a specific fluorophore to be provided to the blood sample that, when excited by an excitation signal 170 including a frequency component of 500 kHz, generates an emission signal 180 with a luminescence lifetime of 100 ns. The blood oxygen level of the blood sample may then be determined from the emission signal 180 based on the expected luminescence lifetime of 100 ns.

A failure to generate an excitation signal 170 that includes the selected frequency component of 500 kHz and to detect the emission signal 180 before the luminescence lifetime of 100 ns expires may result in a failure to accurately determine the blood oxygen level. Further, injecting an inappropriate fluorophore into the blood sample may trigger a different reaction with the characteristic of the blood sample being measured when the sample is excited by the excitation signal 170. Thus, inappropriate fluorophores or excitation signals 170 may result in an emission signal 180 with a measured luminescence lifetime that significantly differs from 100 ns. The resulting luminescence lifetime may in turn prevent the blood oxygen level of the blood sample from being accurately determined.

The excitation and detection device 110 may be configured to generate the excitation signal 170 and detect the emission signal 180. The excitation signal 170 may be provided to the target compound 120 and excite a fluorophore that is exposed to the target compound 120. The emission signal 180 may be generated by the fluorophore in response to being excited by the excitation signal 170. The luminescence lifetime of the fluorophore may be determined by the excitation and detection device 110 based on the received emission signal 180. Thus, in an embodiment of the invention, both generation of the excitation signal 170 and detection of the emission signal 180 may be performed by a single integrated excitation and detection device 110.

The excitation and detection device 110 may generate an excitation signal 170 having a frequency component with a frequency that triggers the fluorophore of the target compound 120 into emitting light having the luminescence lifetime. The excitation and detection device 110 may generate the excitation signal 170 as a periodic waveform or a discrete waveform, and may generate a plurality of excitation signals 170 simultaneously. The excitation and detection device 110 may generate the simultaneous excitation signals 170 as periodic waveforms, discrete waveforms, and/or a combination of periodic and discrete waveforms.

The excitation and detection device 110 may generate the excitation signal 170 as an analog waveform, e.g., as a combination of one or more sine waves. In order to generate the excitation signal 170 at high frequencies, the excitation and detection device 110 may generate the excitation signal 170 via direct digital synthesis. In order for a particular characteristic to be identified, the fluorophore may need to generate an emission signal 180 having a luminescence lifetime that identifies the particular characteristic in response to excitation by the excitation signal 170 at the selected frequency. Advantageously, using an excitation signal 170 including a high frequency component may enable the use of a larger number of fluorophores to generate an emission signal 180 as compared to systems using relatively lower frequencies. This increase in the pool of available fluorophores may be due to use of increased frequency excitation signals 170 enabling the use of fluorophores having shorter luminescence lifetimes.

For example, numerous fluorophores may illuminate in response to excitation by excitation signals including frequency components that exceed 250 kHz. A failure to generate an excitation signal 170 having a sufficiently high frequency component to excite the fluorophores into luminescence may limit the types of fluorophores that can be used to characterize the target compound 120. Limiting the types of fluorophores may in turn limit the type of characteristics that can be identified in the target compound 120. Thus, by generating excitation signals 170 including frequency components that exceed 250 kHz, the excitation and detection device 110 may greatly increase the number of fluorophores that the excitation and detection device 110 can excite. The excitation and detection device 110 may generate the excitation signal 170 at sufficiently high frequencies via direct digital synthesis or using any other signal generation approach that generates the excitation signal 170 at sufficiently high frequencies.

The excitation and detection device 110 may emit the excitation signal 170 into the target compound 120 using the light source 130. The light source 130 may emit the excitation signal 170 at a selected frequency as a light signal that excites the luminescence characteristics of the fluorophore included in the target compound 120 such that the fluorophore generates the emission signal 180 with the luminescence lifetime. The light source 130 may be, for example, a light emitting diode (LED) that emits an excitation signal 170 that is stable across a wide range of temperature operations while requiring low power. Light sources 130 including an LED may require that the excitation signal 170 be provided by the excitation and detection device 110 as an analog waveform. Thus, the excitation and detection device 110 may generate the excitation signal 170 as an analog waveform as described in detail above.

In an alternative embodiment of the invention, the light source 130 may include a laser diode. The laser diode may require that the excitation signal 170 provided by the excitation and detection device 110 be a digital waveform. Thus, the excitation and detection device 110 may generate the excitation signal 170 as a digital waveform. In any case, the light source 130 is not limited to an LED or a laser diode, and may include any other type of light source 130 that can emit an excitation signal 170 which excites the luminescence characteristics of the fluorophore included in the target compound 120.

The excitation signal 170 emitted by the light source 130 may propagate into the target compound 120 via an optical sensor film 160 that interfaces with the target compound 120. The optical sensor film 160 may enable the excitation signal 170 emitted by the light source 130 to propagate into the target compound 120. The optical sensor film 160 may also provide a fluorophore to the target compound 120 that is excited by the excitation signal 170. The optical sensor film 160 may thereby enable the luminescence properties of the fluorophore to be activated by the target compound 120 and excitation signal 170. The optical sensor film 160 may thereby provide an interface between the light source 130 and the target compound 120.

The optical sensor film 160 may also couple the emission signal 180 from the target compound 120 to the excitation and detection device 110. The optical sensor film 160 may enable the emission signal 180 that is generated by luminescence of the fluorophore to propagate from the target compound 120 to the excitation and detection device 110 such that the excitation and detection device 110 may detect the emission signal 180 and determine the luminescence lifetime of the fluorophore.

The excitation and detection device 110 may be configured to measure a phase shift between the emission signal 180 and the excitation signal 170. To this end, the excitation and detection device 110 may detect the luminescence generated by the excited fluorophore as represented by the emission signal 180. The characteristics of the emission signal 180 may depend at least in part on the luminescence lifetime of the fluorophore. The luminescence lifetime of the fluorophore may be considered to have expired when the luminescence generated by the fluorophore drops below a threshold, e.g., the fluorophore no longer generates a detectable emission signal 180.

One approach to determining the luminescence lifetime is to measure the duration of the luminescence lifetime in the time domain. However, numerous fluorophores have luminescence lifetimes less than or equal to what can be detected accurately using this method, e.g., less than or equal to 100 ns. Detecting the duration of luminescence lifetimes with relatively short durations (e.g., below 100 ns) would require electronics that compute at extremely fast rates in order to capture the luminescence lifetime before the fluorophores stop emitting sufficient luminescence. Thus, time-domain based systems may be unable to accurately detect short luminescence lifetimes even with significantly increased costs.

Rather than detecting the duration of the luminescence lifetime in the time domain, the excitation and detection device 110 may measure a phase shift between the emission signal 180 and the excitation signal 170 in the frequency domain. The phase shift between the emission signal 180 and the excitation signal 170 may be dependent upon the luminescence lifetime of the emission signal 180. Thus, the excitation and detection device 110 may measure the phase shift between the emission signal 180 and the excitation signal 170 to determine the luminescence lifetime. The particular characteristics of the target compound 120 that trigger the fluorophore into luminescence when excited by the excitation signal 170 may then be identified based on the phase shift between the emission signal 180 and the excitation signal 170.

Increasing the modulation frequency of the excitation signal 170 in combination with the improved ability to detect short luminescence lifetimes provided by using phase shift measurements may increase the number of fluorophores available for use in analyzing target compounds. Unless fluorophores with short durations are detected before the luminescence lifetime terminates, the luminescence of such fluorophores may go undetected despite the fluorophores illuminating due to the excitation of the excitation signal 170. Thus, the presence of one or more characteristics of a target compound 120 that trigger luminescence of these short-luminescence lifetime fluorophores may go undetected. By allowing the use of fluorophores having short luminescence lifetimes, embodiments of the invention may increase the number of fluorophores that can be used as well as the number of characteristics that can be identified in the target compound 120

The range of frequencies that the excitation and detection device 110 generates in the excitation signal 170 may contribute to the increased range of luminescence lifetimes that can be detected by the excitation and detection device 110. As the frequency of the excitation signal 170 increases, the duration of the luminescence lifetime generated by the emission signal 180 may decrease. The phase shift of the emission signal 180 relative to the excitation signal 170 may be dependent upon the duration of the luminescence lifetime. The excitation and detection device 110 may increase the range of luminescence lifetimes that can be detected by the excitation and detection device 110 by increasing the frequency of the excitation signal 170 and measuring the phase shift between the excitation signal 170 and the emission signal 180. Excitation signals 170 including higher frequency components may enable the excitation and detection device 110 to detect luminescence lifetimes with shorter durations as compared to excitation signals 170 limited to relatively low frequency components.

Referring to Equation 2 below, the fluorophore may be excited by an excitation signal 170 having an intensity that varies at a frequency f. The fluorophore may generate an emission signal 180 at a substantially similar frequency as the frequency f of the excitation signal 170. That is, the intensity of the light generated by the fluorophore vary at a frequency substantially similar to the frequency f of the excitation signal 170. However, the intensity of the emission signal 180 may be phase shifted from that of the excitation signal 170 by a phase shift θ. This phase shift θ may result from the intensity of the emission signal 180 lagging the intensity of the excitation signal. The phase shift θ between the emission signal 180 and the excitation signal 170 may be related to the luminescence lifetime, τ as shown by Equation 1.

$$\tan(\theta) = (2\pi f) \times \tau \qquad \text{Eqn. (2)}$$

The excitation and detection device 110 may decrease the minimum luminescence lifetime that the excitation and detection device 110 can detect by increasing the frequency of the excitation signal 170. This may in turn increase the number of fluorophores that can be used to analyze the target compound 120. For example, numerous fluorophores may generate emission signals 180 with luminescence lifetimes that have durations of 100 ns or less. Excitation signals 170 including frequencies that exceed 250 kHz may enable detection of luminescence lifetimes having durations of 100 ns. In an embodiment of the invention, the excitation and detection device 110 may generate an excitation signal 170 that includes frequencies in the range of 100 Hz to 10 MHz and detect emission signals 180 with luminescence lifetimes both above and below 50 ns.

Advantageously, generating the excitation signal 170 and detecting the emission signal 180 with a single device (e.g., by locating the device on an integrated electronics board) may facilitate detection of luminescence lifetimes of short durations. This improvement may be achieved by a reduced delay between the generation of the excitation signal 170 and the detection of the emission signal 180 as compared to frequency domain fluorescence measurement systems 100 that use separate excitation signal generation and emission signal detection devices. Any additional delay, such as may be caused by separate generation and detection devices, may reduce the ability of the system to detect luminescence lifetimes before the luminescence lifetimes expire.

In an embodiment of the invention, the excitation and detection device 110 may measure the phase shift between the emission signal 180 and the excitation signal 170 (and thereby detect luminescence lifetimes of short durations) by performing a Fast Fourier Transform (FFT) analysis on the emission signal 180. The excitation and detection device 110 may measure the phase shift between the emission signal 180 and the excitation signal 170 by performing a FFT analysis, a Digital Fourier Transform (DFT) analysis, using a phase-lock loop, or using any other suitable approach to determine the phase shift between the emission signal 180 and the excitation signal 170.

The excitation and detection device 110 may also identify several different characteristics of the target compound simultaneously rather than identifying each of several different characteristics individually one at a time. To this end, a plurality of different fluorophores may be provided to the target compound 120 with each fluorophore being excited into luminescence by a different frequency. For example, the excitation and detection device 110 may conduct a blood analysis on a single blood sample where several different chemical or biological characteristics of the blood sample are identified simultaneously rather than determining each characteristic sequentially or by using separate samples.

The excitation and detection device 110 may generate a plurality of excitation signals 170 simultaneously with each excitation signal 170 being modulated with different frequency or using a different wavelength of light. Each of the different frequencies may correspond to a corresponding fluorophore or characteristic to be measured in the target compound 120. Several different fluorophores may also be provided to the target compound. Each of the different fluorophores may exhibit a corresponding luminescence lifetime in response to interaction with a corresponding excitation signal 170 and a corresponding characteristic of the target compound 120. The excitation and detection device 110 may thereby excite each fluorophore into generating an emission signal 180 having a luminescence lifetime dependent on the corresponding characteristics of the target compound 120.

For example, the above described blood analysis may include identification of a calcium level and a sodium level in the single blood sample. Two different fluorophores may be provided to the blood sample, one that fluoresces when excited in the presence of calcium, and another that fluoresces when excited in the presence of sodium. Each different fluorophore may be excited by a corresponding excitation signal 170 and emit an emission signal 180 having a corresponding luminescence lifetime. That is, the excitation and detection device 110 may generates two different excitation signals 170 simultaneously, one that includes a frequency that excites the fluorophore corresponding to calcium, and another that includes a frequency that excites the fluorophore corresponding to sodium.

In response to each fluorophore included in the target compound being simultaneously excited by the corresponding excitation signals 170 incident on the target compound 120, each fluorophore may simultaneously generate a corresponding emission signal 180 each having a luminescence lifetime corresponding to its source fluorophore. The excitation and detection device 110 may simultaneously detect each of the emission signals 180 and simultaneously measure the phase shift between each emission signal 180 and its corresponding excitation signal 170. In simultaneously measuring the phase shift between each emission signal 180 and each corresponding excitation signal 170, the excitation and detection device 110 may simultaneously determine the luminescence lifetime for each fluorophore and in turn identify each of the corresponding characteristics of the target compound 120.

By way of example, one excitation signal 170 including one frequency may be provided to the blood sample to excite the calcium-detecting fluorophore into generating one emission signal 180. The one emission signal may be generated for the duration of the luminescence lifetime of the calcium-detecting fluorophore when the one excitation signal 170 interacts with the calcium and the calcium-detecting fluorophore in the blood sample. Another excitation signal 170 including another frequency may be provided to the blood sample to excite the sodium-detecting fluorophore into generating another emission signal 180. The other emission signal may be generated for the duration of the luminescence lifetime of the sodium-detecting fluorophore when the other excitation signal 170 interacts with the sodium and the sodium-detecting fluorophore in the blood sample.

The excitation and detection device 110 may then simultaneously detect both emission signals 180 being simultaneously generated by the calcium and sodium-detecting fluorophores. The excitation and detection device 110 may then simultaneously compare the phase shift of each emission signal 180 with its corresponding excitation signal 170. Based on the phase shift between each emission signal 180 and its corresponding excitation signal 170, the excitation and detection device 110 may simultaneously determine the luminescence lifetime of the calcium and sodium-detecting fluorophores. The excitation and detection device 110 may thereby simultaneously identify the calcium level of the blood sample as well as the sodium level of the blood sample.

The excitation and detection device 110 may simultaneously identify several different characteristics of the target compound 120. Rather than identify a single characteristic based on the determination of a single phase shift between a single excitation signal 170 and a single emission signal 180 before moving on to identify another characteristic, and so on, the excitation and detection device 110 may identify several different characteristics simultaneously based on the determination of several different phase shifts between several different excitation signals 170 and several different emission signals 180.

It should be understood that the simultaneous generation of more than one excitation signal 170 may trigger more than one emission signal 180, each emission signal 180 may have a different luminescence lifetime, and the excitation and detection device 110 may detect more than one emission signal 180 simultaneously. However, it should be further understood that the excitation and detection device 110 may detect each emission signal 180 as generated but that there may be a lag between different emission signals 180. Thus, the excitation and detection device 110 may determine the phase shift between each emission signal 180 and its corresponding excitation signal 170 as each emission signal 180 is detected, and may determine more than one phase shift simultaneously when more than one emission signal 180 is detected simultaneously.

"Simultaneous detection" may include scenarios in which each step in identifying more than one characteristic of a target compound is executed simultaneously, and may also include any combination of steps being executed simultaneously dependent on the generation of the different emission signals 180. Thus, it should be recognized that simultaneous detection may include measuring of a phase shift between more than one emission signal 180 and more than one excitation signal 170 without having to generate one excitation signal 170, detect the resulting emission signal 180, and determine the phase shift between the two before generating another excitation signal 170, and so on.

Figure 2:
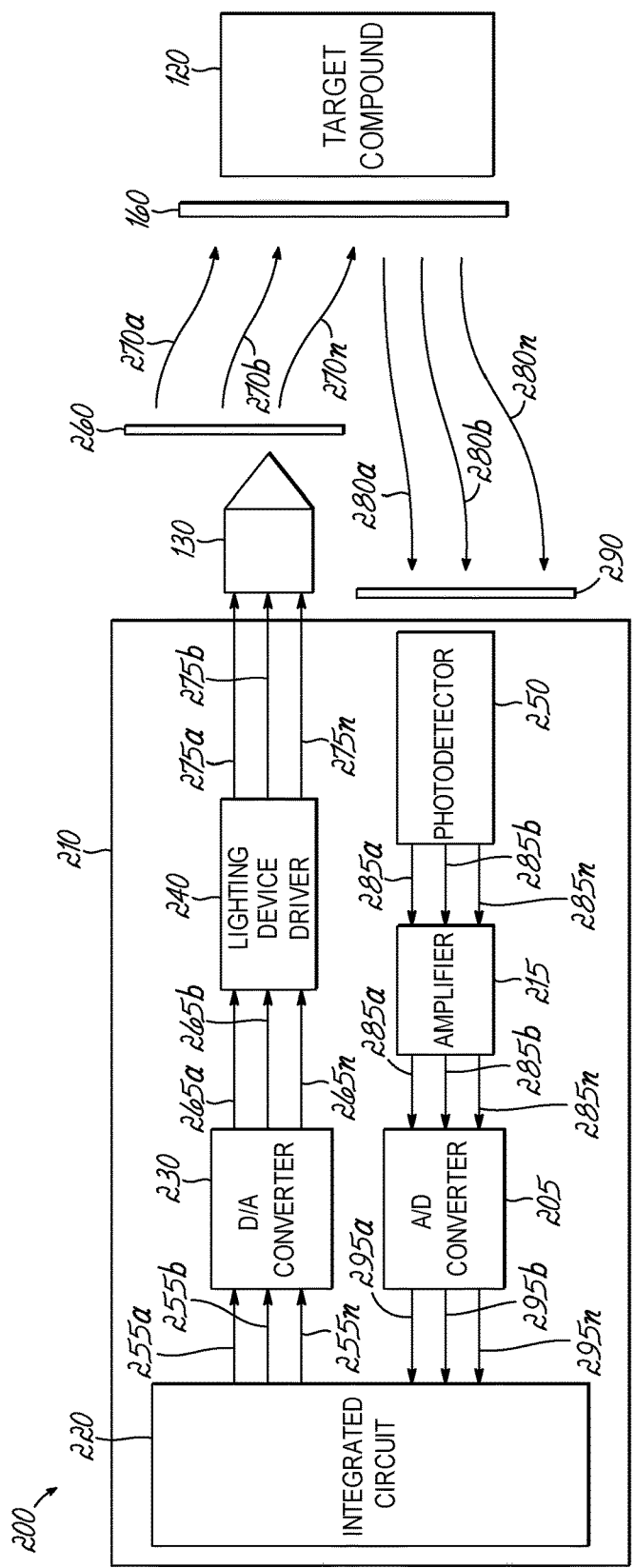
FIG. 2 is a diagrammatic view of another exemplary frequency domain fluorescence measurement system.

Referring now to FIG. 2, an exemplary embodiment of a frequency domain fluorescence measurement system 200 for analyzing a target compound 120 is presented. The frequency domain fluorescence measurement system 200 may include an excitation and detection device 210, the light source 130, a short-pass filter 260, the optical sensor film 160, and a long-pass filter 290. The excitation and detection device 210 may include an integrated circuit 220 having an output operatively coupled to a light source driver 240 by a digital to analog (D/A) converter 230, and a photodetector 250. The photodetector 250 may include an avalanche photodiode, and may output an electrical signal that is operatively coupled to the integrated circuit 220 by an amplifier 215 and an analog to digital (A/D) converter 205.

The excitation and detection device 210 may identify several different characteristics included in the target compound 120 simultaneously. To this end, the excitation and detection device 210 may simultaneously generate a plurality of excitation signals 270(a-n), where n is an integer greater than or equal to one. Each of the different excitation signals 270(a-n) may include a different frequency component, with each frequency component corresponding to a frequency that excites a corresponding fluorophore into luminescence for a corresponding luminescence lifetime. The excitation and detection device 210 may generate each of the different excitation signals 270(a-n) simultaneously, and each of the excitation signals 270(a-n) may include a range of frequencies having high frequency components that exceed 250 kHz.

The excitation and detection device 210 may include an integrated circuit 220 that generates a plurality of source digital signals 255(a-n), where n is an integer that corresponds to the number of excitation signals 270(a-n) generated by the excitation and detection device 210. Each of the source digital signals 255(a-n) generated by the integrated circuit 220 may be a digital representation of a periodic signal that the excitation signals 270(a-n) embody when provided to the target compound 120. For example, each of the source digital signals 255(a-n) generated by the integrated circuit 220 may be a digital representation of a sinusoidal signal having a frequency that corresponds to the specified frequency of a corresponding one of excitation signals 270(a-n).

As another example, the sinusoidal signal may represent a time varying intensity of the light emitted by the excitation and detection device 210. This time varying light may have a fundamental wavelength (e.g., 184, 254, 365, 405, 436, 546, or 578 nm) that provides enough energy to excite the fluorophore into emitting photons at another (e.g., longer) wavelength. The emitted wavelength may be characteristic of the fluorophore or of a combination of the fluorophore and the characteristic of the target compound 120 being evaluated.

The integrated circuit 220 may generate each of the source digital signals 255(a-n) via direct digital synthesis so that each of the source digital signals 255(a-n) is an accurate digital representation of its corresponding sinusoidal signal. The integrated circuit 220 may be an integrated circuit that is configured to generate the different excitation signals 270(a-n) simultaneously, such as a field-programmable array (FPGA), or any other suitable circuit.

The source digital signals 255(a-n) may be provided to the digital to analog (D/A) converter 230. The D/A converter 230 may convert each of the source digital signals 255(a-n) into a corresponding analog signal 265(a-n), where each of the analog signals are the analog representation of the sinusoidal signals represented by the corresponding excitation signals 270(a-n).

The analog signals 265(a-n) may be provided to the light source driver 240. The light source driver 240 may process each of the analog signals 265(a-n) to generate a corresponding analog drive signal 275(a-n) that drives the light source 130. This processing may include, for example, mapping a voltage level of the analog signal 265(a-n) to a drive level that causes the light source 130 to output the corresponding excitation signal 270(a-n) at an intensity proportional to its respective analog signal 265(a-n). For example, the light source driver 240 may generate drive signals 275(a-n) that include the analog representation of the sinusoidal signals which embody each of the corresponding excitation signals 270(a-n) but are elevated in voltage in order to drive the light source 130. Each of the excitation signals 270(a-n) may pass through the short-pass filter 260 and be provided to the target compound 120 via the optical sensor film 160 to excite a corresponding fluorophore into generating a corresponding emission signal 280(a-n) having a luminescence lifetime.

The fluorophores in the target compound 120 may thereby be excited simultaneously into generating emission signals 280(a-n) each having a corresponding luminescence lifetime that results from an interaction of the excitation signal 270(a-n), the fluorophore, and the specific characteristic of the target compound associated with the fluorophore. The luminescence of each of the fluorophores may generate a plurality of emission signals 280(a-n) with n corresponding to the quantity of fluorophores that are illuminated. Each of the emission signals 280(a-n) may be an analog light wave that passes through a long-pass filter 290 before reaching the photodetector 250 of emission and detection device 210.

The photodetector 250 may detect each of the emission signals 280(a-n), and may be based on silicon or any other semiconductor material suitable for detecting the emission signals 280(a-n). The photodetector 250 may be configured to detect each of the emission signals 280(a-n) simultaneously, and may detect each of the emission signals 280(*a-n*) before its luminescence lifetime lapses and terminates the corresponding emission signal 280(*a-n*).

The photodetector 250 may generate the analog signals 285(*a-n*), where n is an integer that corresponds to the quantity of emission signals 280(*a-n*) detected by the photodetector 250. The analog signals 285(*a-n*) may be analog waveforms that correspond to the analog light waves provided by the emission signals 280(*a-n*) as detected by the photodetector 250. The photodetector 250 may provide the analog signals 285(*a-n*) to an amplifier 215 that amplifies the analog signals 285(*a-n*) so that the analog signals 285(*a-n*) may be adequately converted from analog signals to recovered digital signals 295(*a-n*) by the analog to digital (A/D) converter 230. The recovered digital signals 295(*a-n*) may be a digital representation of the emission signals 280(*a n*) initially detected by the photodetector 250, and may be provided to the integrated circuit 220.

The integrated circuit 220 may determine a phase shift between each of the recovered digital signals 295(*a-n*) and its corresponding source digital signal 255(*a-n*). To this end, the integrated circuit 220 may perform an FFT on one or more of the source and recovered digital signals to determine the phase shift between the recovered digital signals 295(*a-n*) and the source digital signals 255(*a-n*). The integrated circuit 220 may be programmed to perform the FFT analysis with sufficient speed to allow the integrated circuit 220 to simultaneously determine the phase shift between all the recovered digital signals 295(*a-n*) and their corresponding source digital signals 255(*a-n*) in order to simultaneously identify several different characteristics of the target compound 120. The integrated circuit 220 may include a FPGA that enables several different phase shifts to be determined simultaneously and decreases the cost of the excitation and detection device 210 as compared to systems lacking an FPGA.

Figure 3:
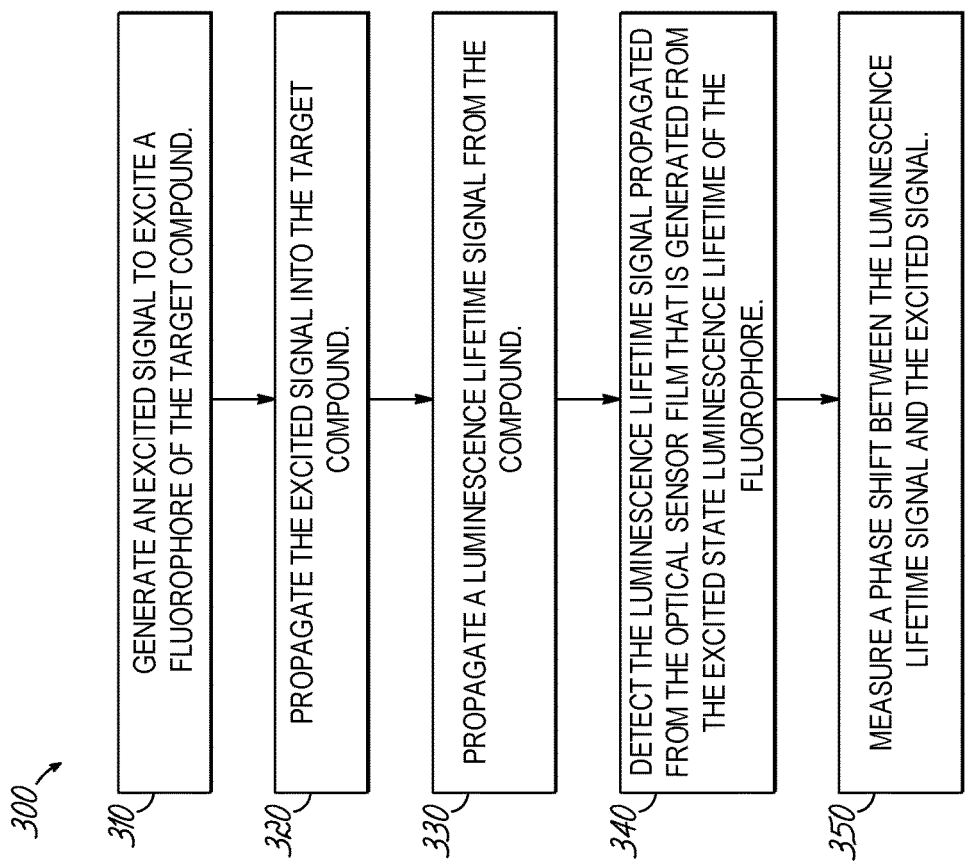
FIG. 3 is a flowchart depicting a process that may be implemented by one or more of the frequency domain fluorescence measurement systems of FIGS. 1 and 2.

FIG. 3 is a flowchart depicting a process 300 that may be executed by the frequency domain fluorescence measurement system 100, 200 in accordance with an exemplary embodiment of the invention.

In block 310, the process 300 may generate an excitation signal configured to excite a fluorophore that has been provided to the target compound.

In block 320, the process 300 may cause the excitation signal to propagate into the target compound. The excitation signal may include a waveform that triggers the fluorophore into generating an emission signal having or otherwise indicative of a luminescence lifetime. The excitation signal 170 may include a specific frequency component that is generated by the excitation and detection device 110. The frequency component of the excitation signal 170 may excite the fluorophore into luminescence when the excitation signal 170 interacts with the fluorophore or characteristic of the target compound 120 at the specific frequency.

In block 330, the process 300 propagates the emission signal from the target compound 120. The emission signal 180 may be propagated from the target compound 120 for the duration of the luminescence lifetime, e.g., for as long as it is being generated by the fluorophore or target compound. In block 340, the process 300 may detect the emission signal 180. The emission signal may be propagated from the optical sensor film, e.g., the emission signal 180 may be propagated from the optical sensor film 160 and detected by the excitation and detection device 110.

In block 350, the process 300 may measure a phase shift between the emission signal and the excitation signal. The phase shift may identify the luminescence lifetime of the fluorophore. For example, the phase shift between the emission signal 180 and the excitation signal 170 may be measured by the excitation and detection device 110. The phase shift may be used to determine the luminescence lifetime of the fluorophore caused by the interaction of the excitation signal 170 at the specified frequency and the characteristic of the target compound 120. Thus, the characteristic included of target compound 120 may be identified from the phase shift between the emission signal 180 and the excitation signal 170.

Figure 4:
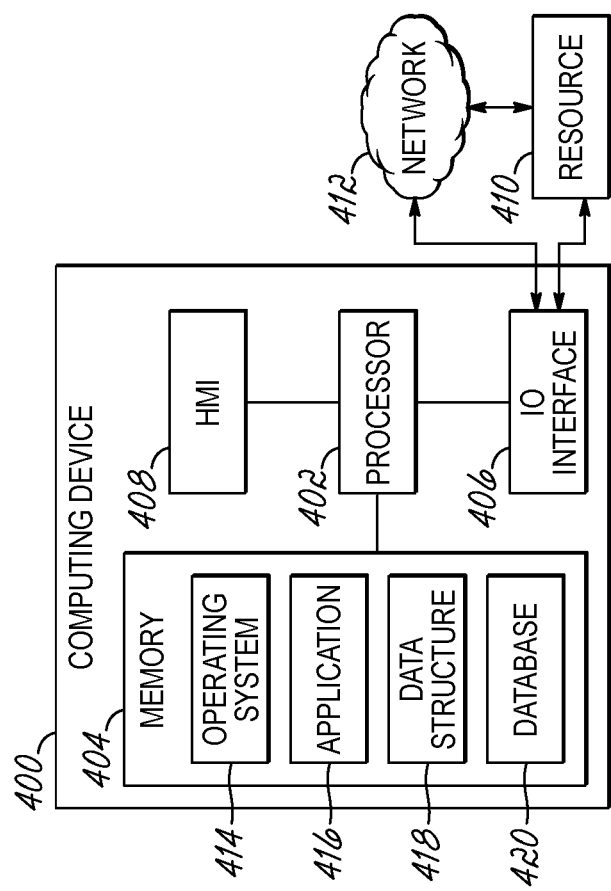
FIG. 4 is a diagrammatic view of a computer that may be used to implement one or more of the components or processes depicted in FIGS. 1-3.

Referring now to FIG. 4, embodiments of the invention described above, or portions thereof, may be implemented using one or more computer devices or systems, such as exemplary computer 400. The computer 400 may include a processor 402, a memory 404, an input/output (I/O) interface 406, and a Human Machine Interface (HMI) 408. The computer 400 may also be operatively coupled to one or more external resources 410 via the network 412 or I/O interface 406. External resources may include, but are not limited to, servers, databases, mass storage devices, peripheral devices, cloud-based network services, or any other resource that may be used by the computer 400.

The processor 402 may include one or more devices selected from microprocessors, micro-controllers, digital signal processors, microcomputers, central processing units, field-programmable gate arrays, programmable logic devices, state machines, logic circuits, analog circuits, digital circuits, or any other devices that manipulate signals (analog or digital) based on operational instructions that are stored in memory 404. Memory 404 may include a single memory device or a plurality of memory devices including, but not limited to, read-only memory (ROM), random access memory (RAM), volatile memory, non-volatile memory, static random access memory (SRAM), dynamic random access memory (DRAM), flash memory, cache memory, or data storage devices such as a hard drive, optical drive, tape drive, volatile or non-volatile solid state device, or any other device capable of storing data.

The processor 402 may operate under the control of an operating system 414 that resides in memory 404. The operating system 414 may manage computer resources so that computer program code embodied as one or more computer software applications, such as an application 416 residing in memory 404, may have instructions executed by the processor 402. In an alternative embodiment, the processor 402 may execute the application 416 directly, in which case the operating system 414 may be omitted. One or more data structures 418 may also reside in memory 404, and may be used by the processor 402, operating system 414, or application 416 to store or manipulate data.

The I/O interface 406 may provide a machine interface that operatively couples the processor 402 to other devices and systems, such as the external resource 410 or the network 412. The application 416 may thereby work cooperatively with the external resource 410 or network 412 by communicating via the I/O interface 406 to provide the various features, functions, applications, processes, or modules comprising embodiments of the invention. The application 416 may also have program code that is executed by one or more external resources 410, or otherwise rely on functions or signals provided by other system or network components external to the computer 400. Indeed, given the nearly endless hardware and software configurations possible, persons having ordinary skill in the art will understand that embodiments of the invention may include applications that are located externally to the computer 400, distributed among multiple computers or other external resources 410, or provided by computing resources (hardware and software) that are provided as a service over the network 412, such as a cloud computing service.

The HMI 408 may be operatively coupled to the processor 402 of computer 400 to allow a user to interact directly with the computer 400. The HMI 408 may include video or alphanumeric displays, a touch screen, a speaker, and any other suitable audio and visual indicators capable of providing data to the user. The HMI 408 may also include input devices and controls such as an alphanumeric keyboard, a pointing device, keypads, pushbuttons, control knobs, microphones, etc., capable of accepting commands or input from the user and transmitting the entered input to the processor 402.

A database 420 may reside in memory 404, and may be used to collect and organize data used by the various systems and modules described herein. The database 420 may include data and supporting data structures that store and organize the data. In particular, the database 420 may be arranged with any database organization or structure including, but not limited to, a relational database, a hierarchical database, a network database, or combinations thereof. A database management system in the form of a computer software application executing as instructions on the processor 402 may be used to access the information or data stored in records of the database 420 in response to a query, which may be dynamically determined and executed by the operating system 414, other applications 416, or one or more modules.

In general, the routines executed to implement the embodiments of the invention, whether implemented as part of an operating system or a specific application, component, program, object, module or sequence of instructions, or a subset thereof, may be referred to herein as "computer program code," or simply "program code." Program code typically comprises computer-readable instructions that are resident at various times in various memory and storage devices in a computer and that, when read and executed by one or more processors in a computer, cause that computer to perform the operations necessary to execute operations or elements embodying the various aspects of the embodiments of the invention. Computer-readable program instructions for carrying out operations of the embodiments of the invention may be, for example, assembly language, source code, or object code written in any combination of one or more programming languages.

Various program code described herein may be identified based upon the application within which it is implemented in specific embodiments of the invention. However, it should be appreciated that any particular program nomenclature which follows is used merely for convenience, and thus the invention should not be limited to use solely in any specific application identified or implied by such nomenclature. Furthermore, given the generally endless number of manners in which computer programs may be organized into routines, procedures, methods, modules, objects, and the like, as well as the various manners in which program functionality may be allocated among various software layers that are resident within a typical computer (e.g., operating systems, libraries, API's, applications, applets, etc.), it should be appreciated that the embodiments of the invention are not limited to the specific organization and allocation of program functionality described herein.

The program code embodied in any of the applications/modules described herein is capable of being individually or collectively distributed as a computer program product in a variety of different forms. In particular, the program code may be distributed using a computer-readable storage medium having computer-readable program instructions thereon for causing a processor to carry out aspects of the embodiments of the invention.

Computer-readable storage media, which is inherently non-transitory, may include volatile and non-volatile, and removable and non-removable tangible media implemented in any method or technology for storage of data, such as computer-readable instructions, data structures, program modules, or other data. Computer-readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store data and which can be read by a computer. A computer-readable storage medium should not be construed as transitory signals per se (e.g., radio waves or other propagating electromagnetic waves, electromagnetic waves propagating through a transmission media such as a waveguide, or electrical signals transmitted through a wire). Computer-readable program instructions may be downloaded to a computer, another type of programmable data processing apparatus, or another device from a computer-readable storage medium or to an external computer or external storage device via a network.

Computer-readable program instructions stored in a computer-readable medium may be used to direct a computer, other types of programmable data processing apparatuses, or other devices to function in a particular manner, such that the instructions stored in the computer-readable medium produce an article of manufacture including instructions that implement the functions, acts, or operations specified in the flow-charts, sequence diagrams, or block diagrams. The computer program instructions may be provided to one or more processors of a general purpose computer, a special purpose computer, or other programmable data processing apparatus to produce a machine, such that the instructions, which execute via the one or more processors, cause a series of computations to be performed to implement the functions, acts, or operations specified in the flow-charts, sequence diagrams, or block diagrams.

In certain alternative embodiments, the functions, acts, or operations specified in the flow-charts, sequence diagrams, or block diagrams may be re-ordered, processed serially, or processed concurrently consistent with embodiments of the invention. Moreover, any of the flow-charts, sequence diagrams, or block diagrams may include more or fewer blocks than those illustrated consistent with embodiments of the invention.

The terminology used herein is for the purpose of describing particular embodiments only and is not intended to be limiting of the embodiments of the invention. As used herein, the singular forms "a", "an" and "the" are intended to include both the singular and plural forms, and the term "or" is intended to include both alternative and conjunctive combinations, unless the context clearly indicates otherwise. It will be further understood that the terms "comprises" or "comprising," when used in this specification, specify the presence of stated features, integers, actions, steps, operations, elements, or components, but do not preclude the presence or addition of one or more other features, integers, actions, steps, operations, elements, components, or groups thereof. Furthermore, to the extent that the terms "includes", "having", "has", "with", "comprised of", or variants thereof are used in either the detailed description or the claims, such terms are intended to be inclusive in a manner similar to the term "comprising".

While all the invention has been illustrated by a description of various embodiments, and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. An apparatus for analyzing a target compound, comprising:
    a light source configured to generate an excitation signal;
    a photodetector configured to receive an emission signal;
    one or more processors operably coupled to the light source and the photodetector and configured to cause the apparatus to:
    transmit the excitation signal into the target compound;
    receive the emission signal from the target compound;
    compare the emission signal to the excitation signal in a frequency domain;
    determine a phase of the emission signal relative to the excitation signal based on the comparison;
    determine a first luminescence lifetime based on the phase of the emission signal; and
    in response to the first luminescence lifetime matching a second luminescence lifetime, determine that the target compound includes a predetermined characteristic.

2. The apparatus of claim 1 further comprising:
    an optical sensor film that includes a fluorophore configured to provide a fluorescent indicator to the target compound, the fluorescent indicator having the second luminescence lifetime in response to the target compound including the predetermined characteristic.

3. The apparatus of claim 1, wherein the target compound includes a fluorophore configured to provide a fluorescent indicator having the second luminescence lifetime in response to the target compound including the predetermined characteristic.

4. The apparatus of claim 1, wherein the one or more processors are further configured to cause the apparatus to:
    generate the excitation signal by providing an analog drive signal to the light source that causes the light source to emit the excitation signal.

5. The apparatus of claim 1, wherein the wherein the one or more processors cause the apparatus to compare the emission signal to the excitation signal in the frequency domain by using a Fast Fourier Transform to transform at least one of the emission signal and the excitation signal from a time domain into the frequency domain.

6. The apparatus of claim 1, wherein the one or more processors are further configured to cause the apparatus to:
    transmit a plurality of excitation signals into the target compound;
    receive a plurality of emission signals from the target compound; and
    for each emission signal received by the apparatus:
    compare the emission signal to its corresponding excitation signal in the frequency domain;
    determine the phase of the emission signal relative to its corresponding excitation signal based on the comparison;
    determine the first luminescence lifetime based on the phase of the emission signal; and
    in response to the first luminescence lifetime matching a corresponding second luminescence lifetime, determine that the target compound includes a corresponding predetermined characteristic.

7. The apparatus of claim 6 further comprising:
    an optical sensor film that includes one or more fluorophores each configured to provide a fluorescent indicator having the second luminescence lifetime in response to the target compound including the predetermined characteristic corresponding to that fluorophore.

8. The apparatus of claim 6 wherein each of the plurality of excitation signals includes a frequency component having a different frequency than the other excitation signals.

9. The apparatus of claim 1, wherein the excitation signal includes a frequency component in a frequency range of 100 Hz to 10 MHz.

10. The apparatus of claim 1, wherein the one or more processors and the photodetector are located on a single chip, and the one or more processors include a field-programmable gate array.

11. A method of analyzing a target compound, comprising:
    transmitting an excitation signal into the target compound;
    receiving an emission signal from the target compound;
    comparing the emission signal to the excitation signal in a frequency domain;
    determining a phase of the emission signal relative to the excitation signal based on the comparison;
    determining a first luminescence lifetime based on the phase of the emission signal; and
    in response to the first luminescence lifetime matching a second luminescence lifetime, determining that the target compound includes a predetermined characteristic.

12. The method of claim 11 further comprising:
    providing a fluorophore to the target compound, the fluorophore being configured to provide a fluorescent indicator having the second luminescence lifetime in response to the target compound including the predetermined characteristic.

13. The method of claim 11 wherein the target compound includes a fluorophore configured to provide a fluorescent indicator having the second luminescence lifetime in response to the target compound including the predetermined characteristic.

14. The method of claim 11 wherein generating the excitation signal comprises:
    providing an analog drive signal to a light source that causes the light source to emit the excitation signal.

15. The method of claim 11 wherein comparing the emission signal to the excitation signal in the frequency domain comprises:
    using a Fast Fourier Transform to transform at least one of the emission signal and the excitation signal from a time domain into the frequency domain.

16. The method of claim 11 further comprising:
    transmitting a plurality of excitation signals into the target compound;
    receiving a plurality of emission signals from the target compound; and for each emission signal received by the apparatus:
  comparing the emission signal to its corresponding excitation signal in the frequency domain;
  determining the phase of the emission signal relative to its corresponding excitation signal based on the comparison;
  determining the first luminescence lifetime based on the phase of the emission signal; and
  in response to the first luminescence lifetime matching a corresponding second luminescence lifetime, determining that the target compound includes a corresponding predetermined characteristic.

17. The method of claim 16 further comprising:
providing one or more fluorophores to the target compound, each fluorophore being configured to provide a fluorescent indicator having the second luminescence lifetime in response to the target compound including the predetermined characteristic corresponding to that fluorophore.

18. The method of claim 16 wherein each of the plurality of excitation signals includes a frequency component having a different frequency than the other excitation signals.

19. The method of claim 11, wherein the excitation signal includes a frequency component in a frequency range of 100 Hz to 10 MHz.

20. A computer program product for analyzing a target compound, comprising:
  a non-transitory computer-readable storage medium; and
  program code stored on the non-transitory computer-readable storage medium that, when executed by one or more processors, causes the one or more processors to:
  transmit an excitation signal into the target compound;
  receive an emission signal from the target compound;
  compare the emission signal to the excitation signal in a frequency domain;
  determine a phase of the emission signal relative to the excitation signal based on the comparison;
  determine a first luminescence lifetime based on the phase of the emission signal; and
  in response to the first luminescence lifetime matching a second luminescence lifetime, determine that the target compound includes a predetermined characteristic.

* * * * *